(12) United States Patent
Jeong et al.

(10) Patent No.: US 12,015,890 B2
(45) Date of Patent: Jun. 18, 2024

(54) ANTI-SWELLING STRUCTURE OF COVER, AND DEVICE HAVING WATERPROOF STRUCTURE

(71) Applicant: LG ELECTRONICS INC., Seoul (KR)

(72) Inventors: Hwoasu Jeong, Seoul (KR); Yonggeun Jin, Seoul (KR); Joonwon Bhang, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 197 days.

(21) Appl. No.: 17/432,861

(22) PCT Filed: Feb. 21, 2020

(86) PCT No.: PCT/KR2020/002560
§ 371 (c)(1),
(2) Date: Aug. 20, 2021

(87) PCT Pub. No.: WO2020/171654
PCT Pub. Date: Aug. 27, 2020

(65) Prior Publication Data
US 2022/0070566 A1    Mar. 3, 2022

Related U.S. Application Data

(60) Provisional application No. 62/809,371, filed on Feb. 22, 2019.

(51) Int. Cl.
H04R 1/02         (2006.01)
A46B 13/02        (2006.01)

(52) U.S. Cl.
CPC ............ *H04R 1/028* (2013.01); *A46B 13/023* (2013.01); *H04R 1/025* (2013.01); *H04R 1/026* (2013.01); *A46B 2200/1006* (2013.01)

(58) Field of Classification Search
CPC ........ H04R 1/028; H04R 1/025; H04R 1/026; A46B 13/023; A46B 2200/1006
USPC ......................................................... 381/332
See application file for complete search history.

(56) References Cited

U.S. PATENT DOCUMENTS

| 10,172,763 | B2  | 1/2019  | Choi |
| 2007/0081691 | A1 | 4/2007 | Park et al. |
| 2011/0261986 | A1* | 10/2011 | Murayama ............... H04R 1/02 220/9.1 |
| 2015/0271583 | A1 | 9/2015 | Wan |

(Continued)

FOREIGN PATENT DOCUMENTS

| CN | 1946245 A | 4/2007 |
| CN | 203734963 U | 7/2014 |

(Continued)

*Primary Examiner* — Sean H Nguyen
(74) *Attorney, Agent, or Firm* — Birch, Stewart, Kolasch & Birch, LLP

(57) ABSTRACT

Discussed is a device including a case having a receiving space formed therein; a cover configured to surround the case; a speaker assembly configured to be mounted on the case, the speaker assembly including a speaker, a diaphragm, and a resonator formed on one side of the speaker; and a speaker hole configured to be connected to the speaker assembly, wherein the case includes at least one opening formed between the resonator and a space between the cover and the case.

15 Claims, 13 Drawing Sheets

(56) References Cited

U.S. PATENT DOCUMENTS

| | | | |
|---|---|---|---|
| 2018/0081406 A1* | 3/2018 | Kita | H04R 9/08 |
| 2020/0045398 A1* | 2/2020 | Wu | H04R 1/025 |
| 2022/0078558 A1* | 3/2022 | Jiang | H04R 1/025 |

FOREIGN PATENT DOCUMENTS

| | | |
|---|---|---|
| CN | 105640405 A | 8/2016 |
| CN | 106163671 A | 11/2016 |
| CN | 206120217 U | 4/2017 |
| CN | 206506808 U | 9/2017 |
| CN | 206650842 U | 11/2017 |
| CN | 207354604 U | 5/2018 |
| CN | 108430015 A | 8/2018 |
| CN | 208491921 U | 2/2019 |
| JP | 11-155181 A | 6/1999 |
| KR | 10-1470281 B1 | 12/2014 |
| KR | 10-1480515 B1 | 1/2015 |
| KR | 10-2015-0049292 A | 5/2015 |
| KR | 10-2015-0060208 A | 6/2015 |
| KR | 10-1810804 B1 | 1/2018 |
| KR | 10-1848623 B1 | 4/2018 |
| KR | 10-1852410 B1 | 4/2018 |
| KR | 10-2018-0128818 A | 12/2018 |
| WO | WO2017/070163 A1 | 4/2017 |

* cited by examiner

[Fig. 4]
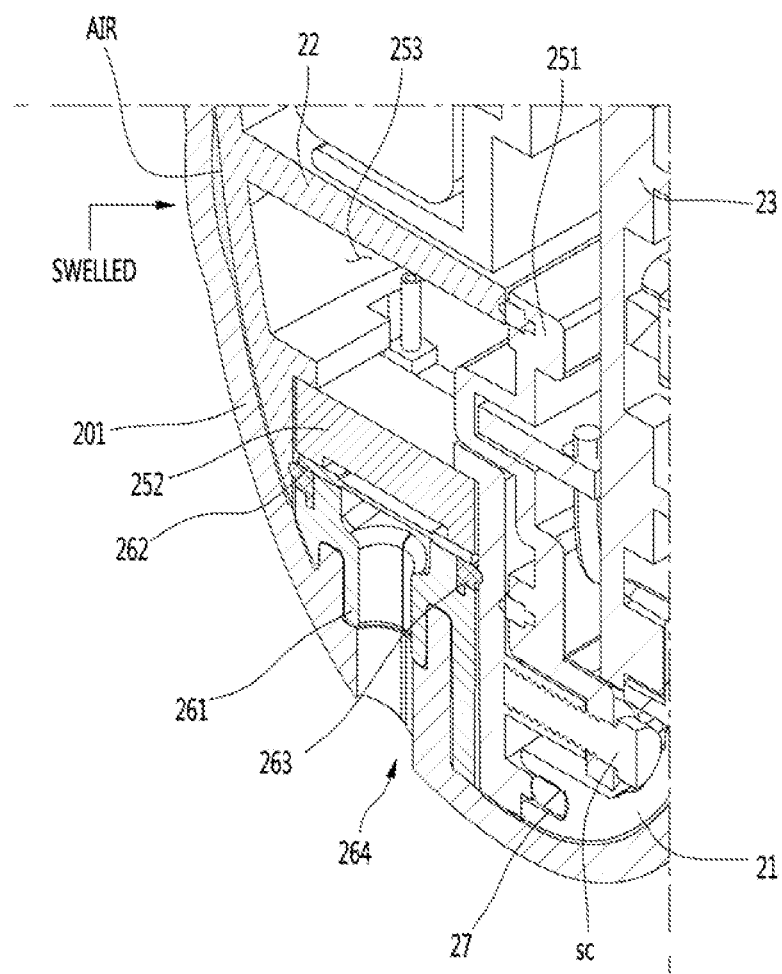

[Fig. 5]
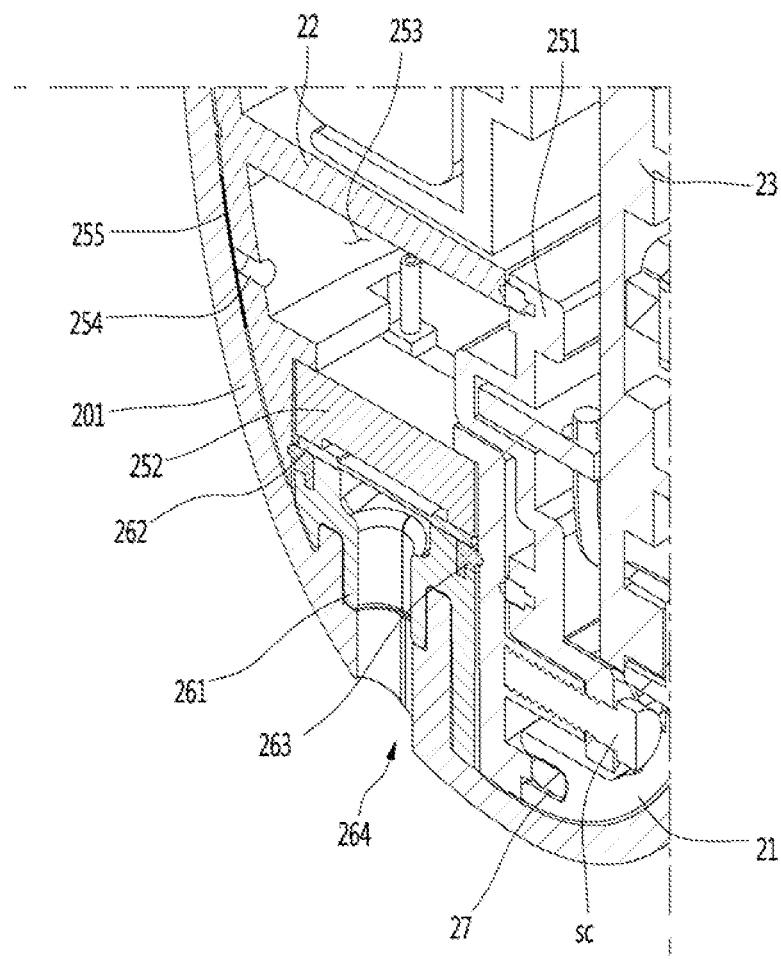

[Fig. 6]
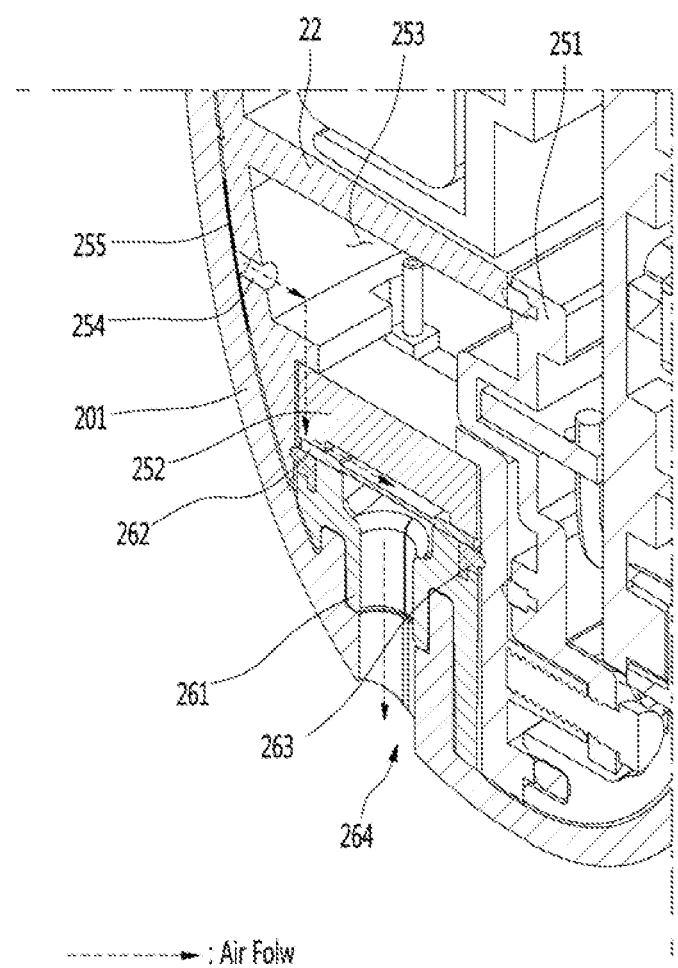
----- : Air Folw

[ Fig. 7]
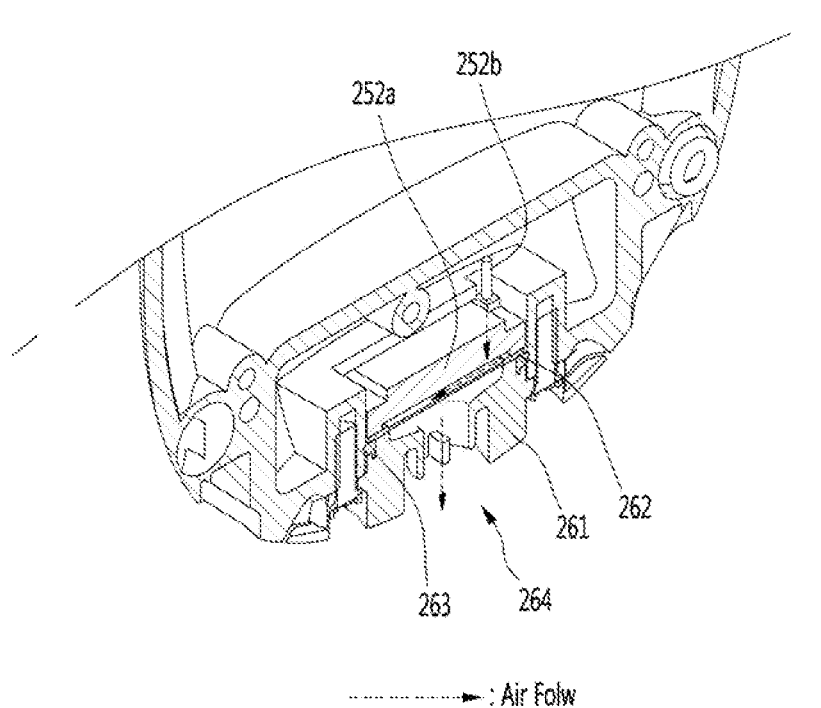

[Fig. 8]
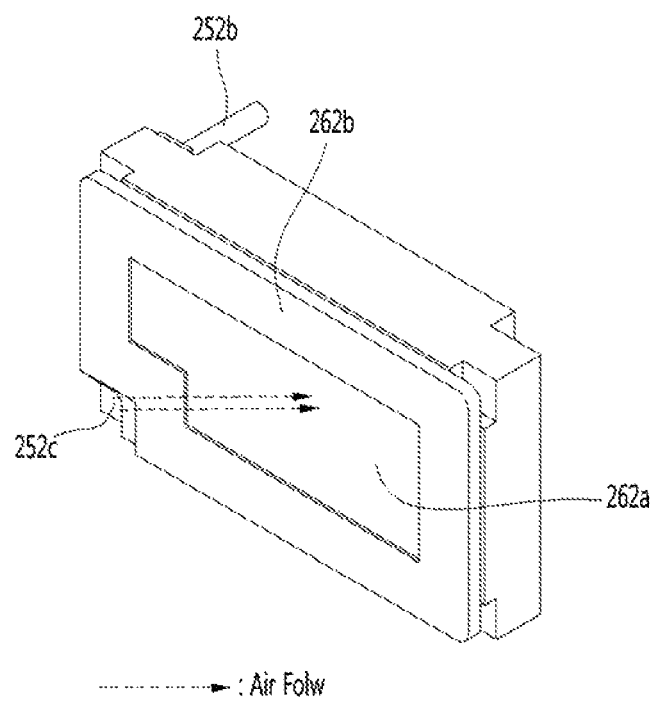

[Fig. 9]
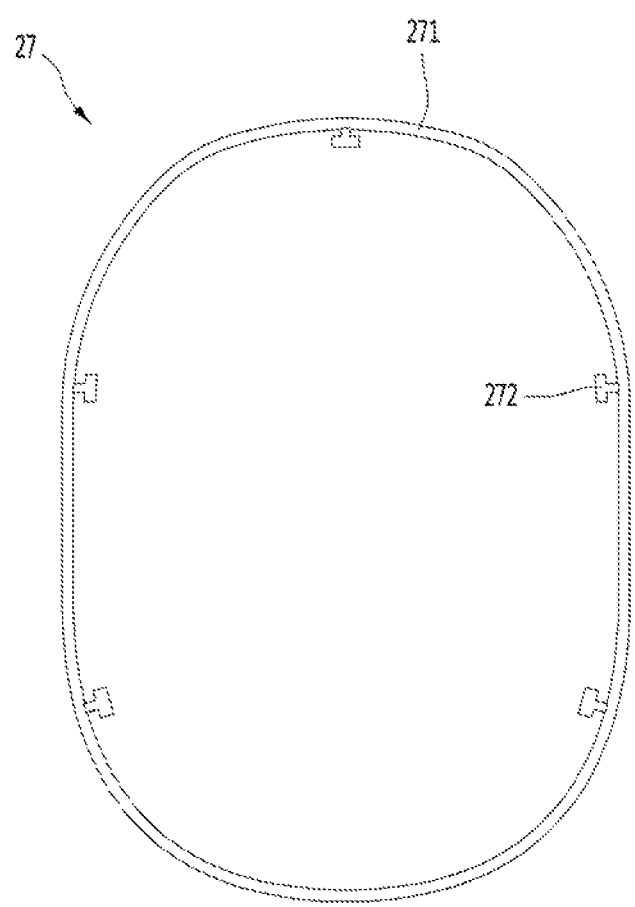

[Fig. 10]
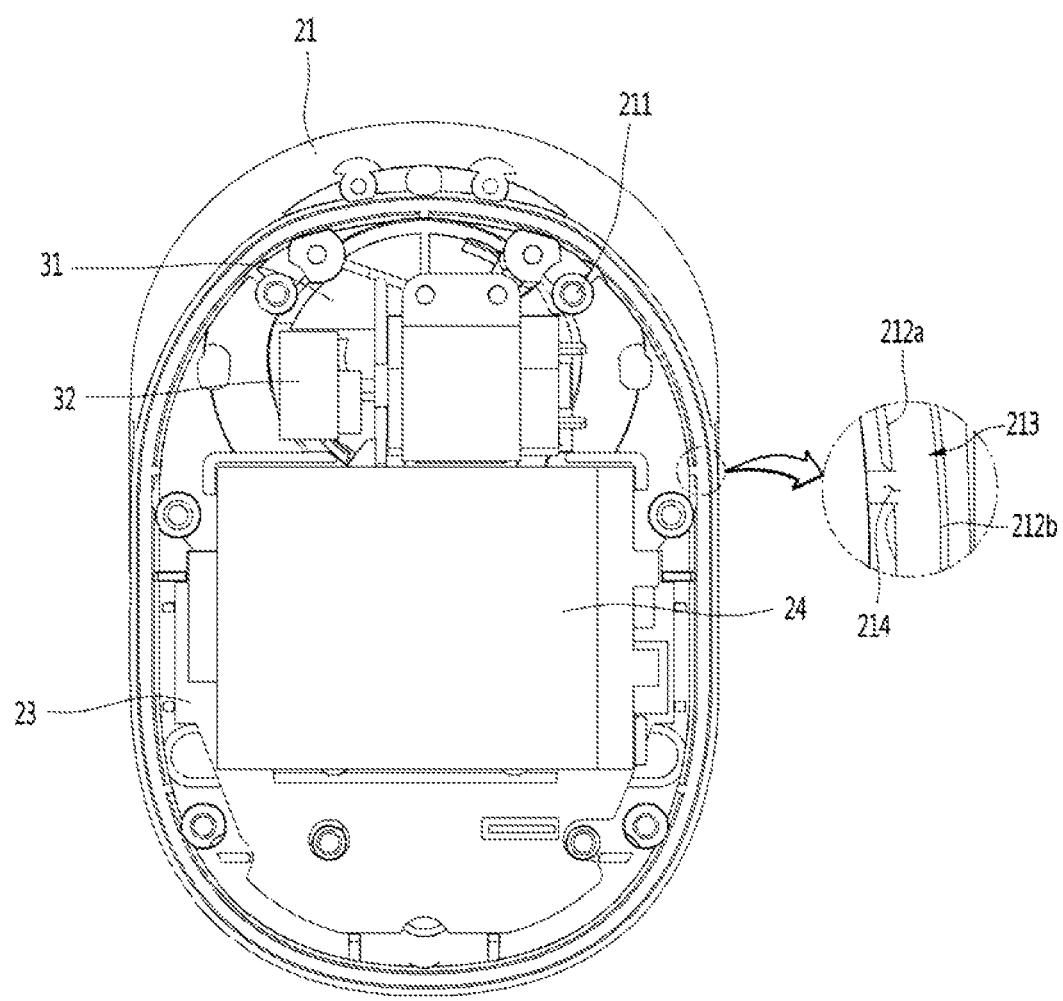

[Fig. 11]
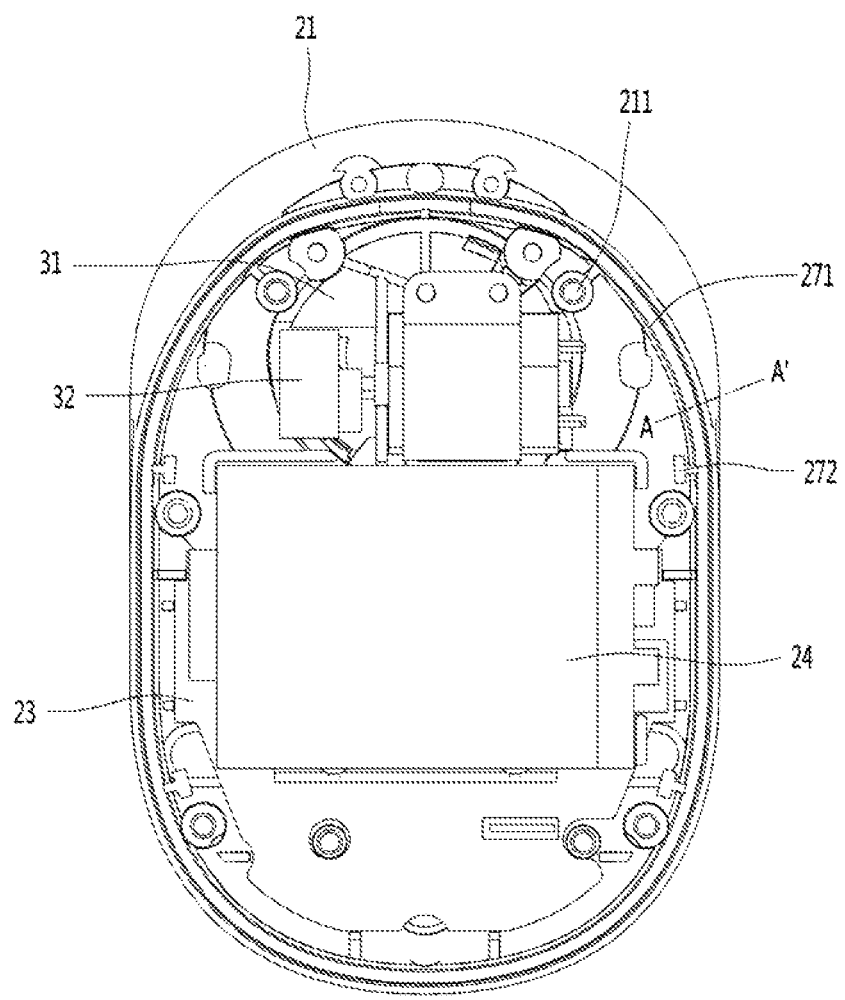

[Fig. 12]
(a) 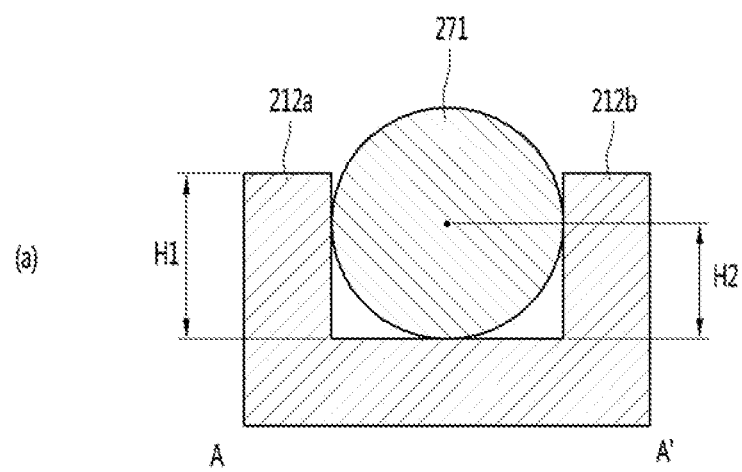
(b) 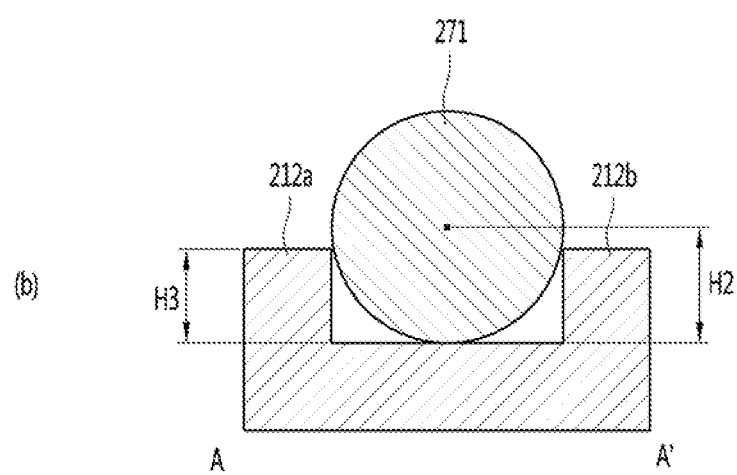

[Fig. 13]
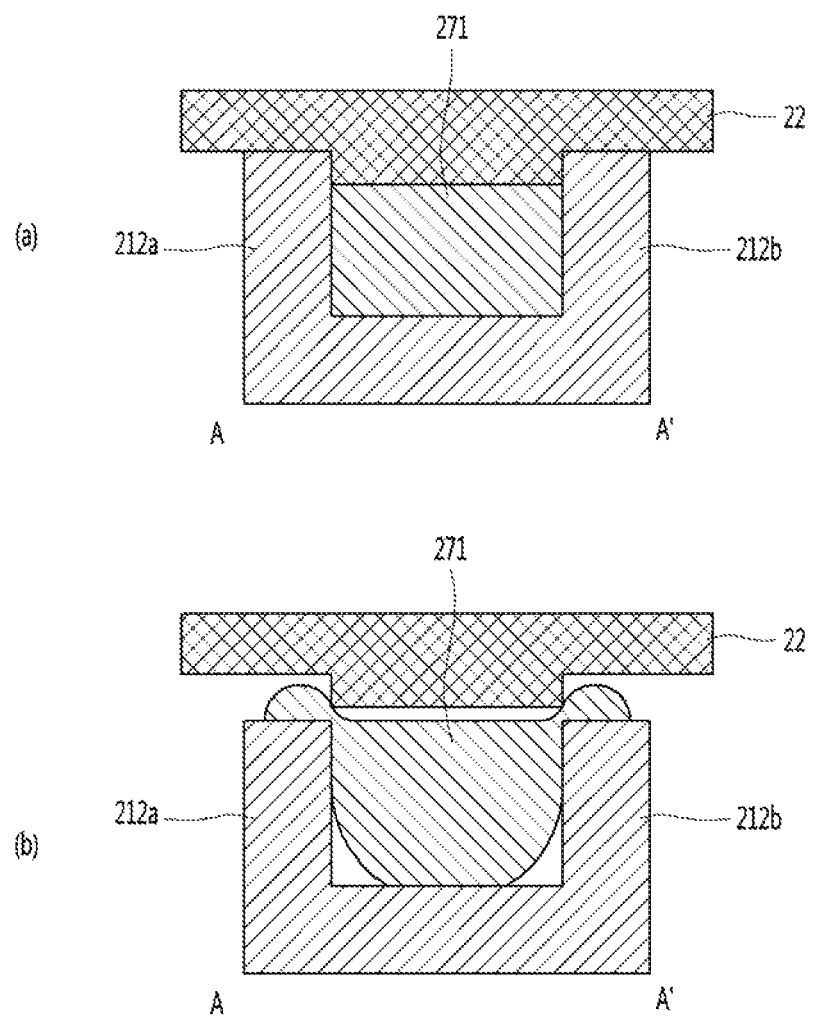

ANTI-SWELLING STRUCTURE OF COVER, AND DEVICE HAVING WATERPROOF STRUCTURE

CROSS REFERENCE TO RELATED APPLICATIONS

This application is the National Stage filing under 35 U.S.C. 371 of International Application No. PCT/KR2020/002560, filed on Feb. 21, 2020, which claims the benefit under 35 U.S.C. § 119(e) to U.S. Provisional Application No. 62/809,371, filed on Feb. 22, 2019, the contents of all these applications are hereby expressly incorporated by reference into the present application.

TECHNICAL FIELD

The present disclosure relates to a device having an anti-swelling structure and a waterproof structure of a cover.

BACKGROUND ART

Recently, various types of devices used in an environment where moisture such as water exists have appeared. For example, in a case of a cleanser that is in contact with the user's skin to remove waste, the cleanser is inevitably in contact with moisture present in the skin when used.

In general, a device may include a case for receiving various chips, circuits, batteries, and the like. The case may be implemented with a hard material such as plastic and metal to protect the parts received in the case.

Such a case may be implemented by combining two or more partial cases to receive the parts in the case. In this case, a micro gap may exist between the combined surfaces of the case, due to process deviation, deviation in the combined surfaces between partial cases, or the like during assembly, and if moisture permeates into the gap, the parts received in the case may be damaged and thus the device may not operate normally.

Meanwhile, such a device may further include a cover surrounding the case in order to protect the case or parts in the case. The cover may be implemented with a material such as silicone and rubber to effectively protect the case from external impact and to suppress permeation of moisture into the case.

DISCLOSURE

Technical Problem

An object to be solved by the present disclosure is to provide a device having a structure that prevents a phenomenon in which the cover swells due to air expansion between a case and a cover.

Another object to be solved by the present disclosure is to provide a device that prevents deterioration of waterproof performance by minimizing the deviation by position of a sealing member provided for waterproofing inside the device.

Technical Solution

The device according to an embodiment of the present disclosure includes at least one opening connecting a space between a space between a case and a cover surrounding the case and a resonator of a speaker assembly, so that air expanded in the space between the cover and the case can be discharged to outside through the resonator.

The at least one opening may be formed at a position corresponding to between the cover and the resonator.

According to an embodiment, a first membrane made of a moisture-permeable and waterproof material may be provided in a region including the at least one opening.

According to an embodiment, the device may further include a speaker cover having an opening corresponding to a speaker hole connected to the speaker assembly.

According to an embodiment, a second membrane made of a moisture-permeable and waterproof material may be provided between the speaker cover and the speaker assembly.

The second membrane may be divided into a permeable region and a contact region formed outside the permeable region, and the permeable region may be spaced apart from the speaker main body of the speaker assembly by a predetermined distance.

According to an embodiment, a gap region between the speaker main body and the permeable region may be connected to the resonator through a groove formed in the speaker main body or a space between the speaker and the case.

According to an embodiment, the cover may be implemented with a material having higher ductility than the case.

According to an embodiment, the case includes a first case and a second case fastened to the first case to form a receiving space therein, and a sealing member may be mounted between the first case and the second case.

A mounting groove in which the sealing member is mounted may be formed in the first case or the second case.

The sealing member may include a ring-shaped sealing member main body corresponding to the mounting groove, and a plurality of sealing member mounting ribs protruding inward or outward from each of a plurality of points of the sealing member main body.

A plurality of rib mounting guides corresponding to the plurality of sealing member mounting ribs may be formed in the mounting groove.

According to an embodiment, a depth of the mounting groove may be at least half of a cross-sectional height of the sealing member main body.

According to an embodiment, the device further includes an ultrasonic vibrator, a vibration motor, and a brush, and an opening through which at least a part of the ultrasonic vibrator received in the receiving space passes may be formed in the case, and the brush may be fastened to the case and may have a donut shape surrounding a circumference of the ultrasonic vibrator.

Advantageous Effect

According to an embodiment of the present disclosure, at least one opening is formed between the space between the cover surrounding the case and the case and the resonator of the speaker assembly, so that the air that expands in the space between the cover and the case due to temperature changes or the like may be discharged to the outside through the at least one opening and the resonator Accordingly, a phenomenon in which the cover swells due to the expansion of the air is prevented, and the reliability of the product can be guaranteed.

In addition, a plurality of ribs are formed in the ring-shaped sealing member mounted between the front case and the rear case, and a plurality of rib mounting guides corresponding to the plurality of ribs are implemented in the mounting groove formed in the front case or the rear case, and thus the sealing member can be mounted in the correct position of the mounting groove. Accordingly, the deterioration of waterproof performance due to the deviation of the sealing member for each position or the deviation of the sealing member for each product can be minimized.

DESCRIPTION OF DRAWINGS

FIG. 4 is an exemplary view illustrating the swelling phenomenon of the cover that occurs when the anti-swelling structure of the cover is not implemented according to an embodiment of the present disclosure.

FIG. 5 is a view for explaining the anti-swelling structure of the cover according to an embodiment of the present disclosure.

FIG. 6 is a view illustrating a state where air expanding between a cover and a case is discharged to the outside when the anti-swelling structure of FIG. 5 is implemented.

FIG. 7 is a view illustrating a state where air is discharged to the outside through a speaker assembly and a speaker hole provided in a device according to an embodiment of the present disclosure.

FIG. 8 is a view illustrating a membrane for preventing external moisture from permeating into the device while discharging air inside the device to the outside through the speaker hole.

FIG. 9 is a view illustrating a sealing member constituting a waterproof structure of a device according to an embodiment of the present disclosure.

FIG. 10 is a view for explaining a sealing member mounting part formed in the case of the device.

FIG. 11 is a view illustrating a state where the sealing member is mounted to the sealing member mounting part illustrated in FIG. 10.

FIGS. 12 to 13 are views illustrating modified examples of the sealing member according to the height of the mounting groove of the sealing member mounting part.

BEST MODE

Figure 1:
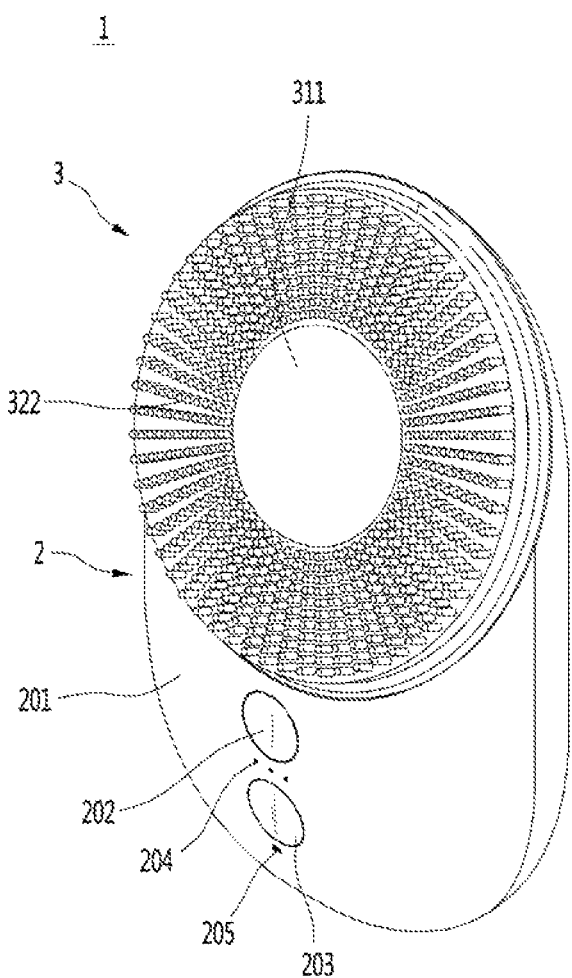
FIG. 1 is a perspective view illustrating a skin cleanser as an example of a device having an anti-swelling structure and a waterproof structure of a cover according to an embodiment of the present disclosure.

Hereinafter, the embodiments disclosed in the present specification will be described in detail with reference to the accompanying drawings, but the same or similar components are assigned the same reference numerals regardless of reference numerals, and overlapping descriptions thereof will be omitted. The suffixes "module" and "part" for the components used in the following description are given or mixed in consideration of only the ease of writing the specification, and do not have distinct meanings or roles by themselves. In addition, in describing the embodiments disclosed in the present specification, if it is determined that detailed descriptions of related known technologies may obscure the subject matters of the embodiments disclosed in the present specification, the detailed description thereof will be omitted. In addition, it should be understood that the accompanying drawings are only for easy understanding of the embodiments disclosed in the present specification, and the technical spirit disclosed herein is not limited by the accompanying drawings, and all changes, equivalents, and substitutes included in the spirit and the technical scope of the present disclosure are included.

Terms including an ordinal number, such as first and second, may be used to describe various components, but the components are not limited by the terms. The above terms are used only for the purpose of distinguishing one component from another.

When a component is referred to as being "connected" or "accessed" to another component, it should be understood that the component may be directly connected or accessed to another component, but there may be other components in between. On the other hand, when it is said that a component is "directly connected" or "directly accessed" to another element, it should be understood that there are no other component in between.

The singular expression includes the plural expression unless the context clearly dictates otherwise.

It should be understood that, in the present application, terms such as "comprises" and "have" are intended to designate that a feature, number, step, operation, component, part, or combination thereof described in the specification exists, but this does not preclude the possibility of the existence or addition of one or more other features, numbers, steps, operations, components, parts, or combinations thereof.

Hereinafter, embodiments of the present disclosure will be described in detail with reference to the accompanying drawings in the present specification.

Figure 2:
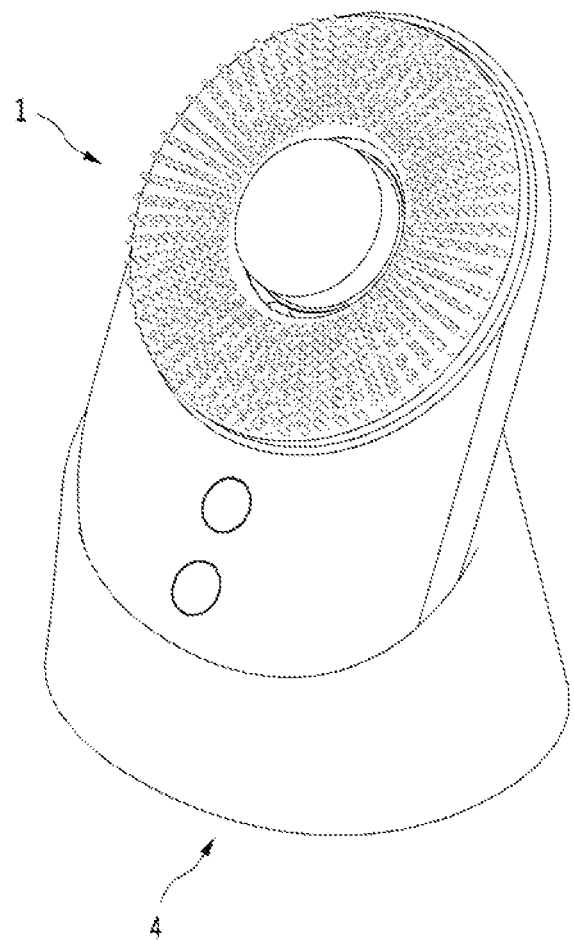
FIG. 2 is a perspective view illustrating a package including the skin cleanser and a cradle illustrated in FIG. 1.

FIG. 1 is a perspective view illustrating a skin cleanser as an example of a device having an anti-swelling structure and a waterproof structure of a cover according to an embodiment of the present disclosure. FIG. 2 is a perspective view illustrating a package including the skin cleanser and a cradle illustrated in FIG. 1.

Referring to FIGS. 1 and 2, a device having an anti-swelling structure and a waterproof structure of a cover according to an embodiment of the present disclosure may include various types of devices. In the present specification, it is assumed that the device is the skin cleanser 1, but the type of the device is not limited thereto.

The skin cleanser 1 may be a device that cleans the skin by contacting the user's skin or massages the skin by applying a certain stimulus to the skin. The skin cleanser 1 may be implemented as a portable skin cleanser that can be used without an external power connection by having a battery therein. In this case, the skin cleanser 1 may be mounted on a cradle 4 during storage or charging.

The skin cleanser 1 may include a main body 2 and a head 3.

The main body 2 may have a shape in which the user can easily clean the skin or massage the skin by holding the main body by hand and being the vibrator 311 and the brush 322 of the head 3 in close contact with the skin. As an example, at least one surface of the main body 2 is formed to be rounded, so that the user can easily grasp the main body 2 by hand.

A receiving space for receiving various parts (circuits, chips, batteries, or the like) may be formed inside the main body 2, and the cover 201 is formed to surround the receiving space, so that the parts inside the receiving space can be protected.

According to an embodiment, the cover 201 may be implemented with a material for preventing moisture, such as water, from permeating into the receiving space. For example, the cover 201 may be implemented as a cover made of a silicon material, but is not limited thereto.

In addition, at least one button 202, 203 for user manipulation is provided on one surface of the main body 2, and at least one indicator 204, 205 for notifying the operating state or battery state of the skin cleanser 1 may be provided.

For example, at least one button 202, 203 may include a first button 202 for turning on/off the power of the skin cleanser 1 and a second button 203 for changing the operation mode (vibration intensity or the like) of the skin cleanser 1.

The at least one indicator 204, 205 may be implemented in a form to transmit light emitted from the light source to the outside by being formed at a position corresponding to the at least one light source provided inside the main body 2. For example, at least one indicator 204, 205 may include a first indicator 204 that notifies whether the skin cleanser 1 is powered on/off or information related to a currently set operation mode, and a second indicator 205 that notifies information related to the battery state of the skin cleanser 1.

The head 3 may be formed on a portion of one surface (for example, the front surface) of the main body. The head 3 forms a contact surface with the skin, so that a predetermined physical stimulus can be applied to the skin. For example, the head 3 may include a vibrator 311 for applying ultrasonic vibrations to the skin, and a brush 322 for applying micro-vibrations. For example, as illustrated in FIG. 1, the brush 322 may be implemented in the form of a ring or donut surrounding the outside of the vibrator 311, but this is not necessarily the case.

Hereinafter, components included in the skin cleanser 1 will be described in more detail with reference to FIG. 3.

Figure 3:
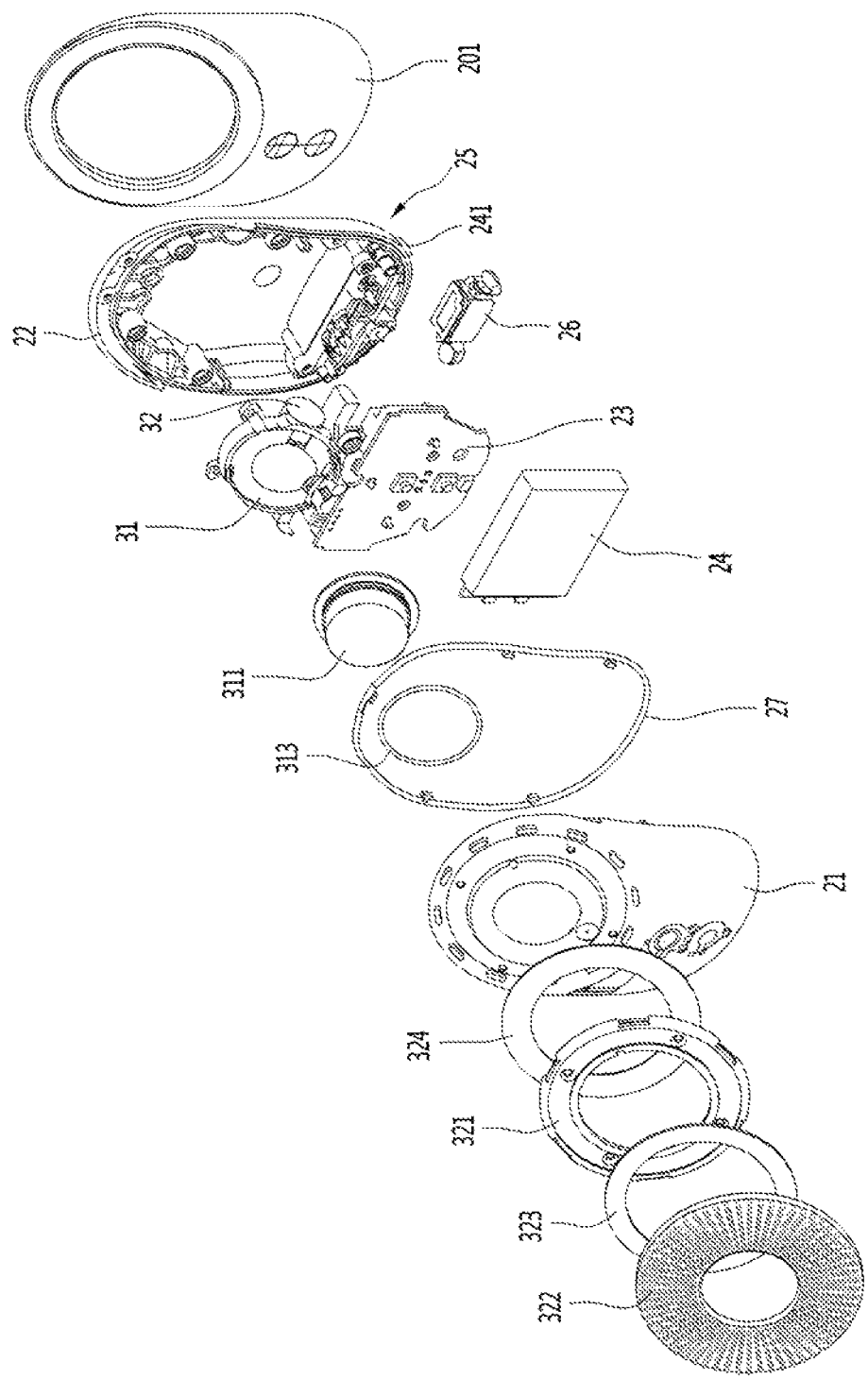
FIG. 3 is an exploded view illustrating the skin cleanser illustrated in FIG. 1.

FIG. 3 is an exploded view illustrating the skin cleanser illustrated in FIG. 1.

In the following drawings, the direction in which the vibrator 311 and the brush 322 face is defined as the front, the portion where the head 3 is disposed is defined as the upper portion, and the portion where the speaker assembly 25 is disposed is defined as the lower portion.

Referring to FIG. 3, the main body 2 may include a cover 201, a front case 21, a rear case 22, a substrate 23, a battery 24, a speaker assembly 25, a speaker cover assembly 26, a sealing member 27, and the like.

The cover 201 may be formed to surround at least a portion of the front case 21 and the rear case 22. The inner surface of the cover 201 may be in close contact with the outer surfaces of the front case 21 and the rear case 22. As described above, the cover 201 may be implemented with a material such as silicon to prevent moisture from permeating into the main body 2.

The front case 21 may form a front surface of the main body 2, and the rear case 22 may form a rear surface of the main body 2. The front case 21 and the rear case 22 may be fastened to each other through a plurality of fastening members (for example, screws or the like). As the front case 21 and the rear case 22 are fastened, receiving spaces in which the components such as a substrate 23, a battery 24, and a speaker assembly 25 are received may be formed inside the front case 21 and the rear case 22. The front case 21 and the rear case 22 may be implemented with a material such as plastic.

In addition, some components of the head 3 may be received in the receiving space formed by the front case 21 and the rear case 22. For example, a portion of the vibrator 311, the bracket 31, and the vibration motor 32 may be received in the receiving space.

An opening through which a portion of the vibrator 311 passes may be formed in the front case 21. A portion of the vibrator 311 received in the receiving space may be exposed to the outside through the opening to form a contact surface with the skin.

Meanwhile, a region adjacent to the opening (or surrounding the opening) of the outer surface of the front case 21 may form a mounting region of the brush bracket 321.

In addition, at least one opening may be further formed in the front case 21 at a position corresponding to at least one button and/or at least one light source provided on the substrate 23.

At least one component included in the speaker assembly 25 may be fastened to the rear case 22. According to an embodiment, a space corresponding to a resonator 253 (refer to FIG. 4) of the speaker assembly 25 may be formed in the rear case 22. A speaker hole for emitting the sound generated by the speaker assembly 25 to the outside is formed in the lower side of the rear case 22, and the speaker cover assembly 26 may be mounted in the speaker hole. Contents related to the speaker assembly 25 and the speaker cover assembly 26 will be described in more detail later with reference to FIGS. 4 to 8.

According to an embodiment, at least one power connection terminal 241 may be further formed on the lower side of the rear case 22. The power connection terminal 241 may be electrically connected to the battery 24. An opening may be formed in an area of the cover 201 corresponding to the power connection terminal 241, and the power connection terminal 241 may be exposed to the outside through the opening. When the skin cleanser 1 is mounted on the cradle 4, the power connection terminal 241 may be in contact with a power supply terminal (not illustrated) provided in the cradle 4 to receive power from the outside. The supplied power is provided to the battery 24 so that the battery 24 can be charged.

The substrate 23 may be received in an receiving space between the front case 21 and the rear case 22. The substrate 23 may be fastened and fixed to at least one of the front case 21 and the rear case 22. The substrate 23 may be provided with various control configurations related to the operation of the skin cleanser 1. For example, the control components may include a processor, a memory, a communication circuit (communication interface), an input interface (button, or the like), an output interface (light source or the like). The processor may be connected to the speaker assembly 25, the vibrator 311, and the vibration motor 32 to control respective operations thereof.

A battery 24 may be provided at the rear of the substrate 23. The battery 24 may be mounted and fixed to the rear case 22 or the rear surface of the substrate 23. The battery 24 may supply power for the operation of the skin cleanser 1 to each component. As described above, the battery 24 may receive power for charging from the outside through the power connection terminal 241 as the skin cleanser 1 is mounted on the cradle 4.

According to an embodiment, a sealing member 27 may be provided between the front case 21 and the rear case 22. For example, an edge region of each of the front case 21 and the rear case 22 may form a contact region during fastening. As illustrated, the contact region may correspond to a closed curve shape (for example, an ellipse or the like), and the sealing member 27 may be implemented in a closed curve ring shape corresponding to the contact region.

The sealing member 27 seals a gap generated in the contact region when the front case 21 and the rear case 22 are fastened, thereby preventing moisture from permeating into the inside through the gap.

Meanwhile, the sealing member 27 according to the embodiment of the present disclosure is implemented to minimize the thickness deviation according to the position during assembly, thereby preventing the deterioration of the waterproof performance. The related contents will be described in more detail later with reference to FIGS. 9 to 13.

With continued reference to FIG. 3, the head 3 may include a bracket 31, a vibrator 311, a vibration motor 32, a brush bracket 321, and a brush 322.

The bracket 31 may be fastened to the front case 21 and/or the rear case 22 to be received in an receiving space between the front case 21 and the rear case 22.

The vibrator 311 may be mounted on the front of the bracket 31, and the vibration motor 32 may be mounted on the rear side of the bracket 31.

The vibrator 311 may have a disk shape having a predetermined height. The bottom surface of the vibrator 311 is mounted on the bracket 31 and can be located in the receiving space, and the top surface of the vibrator 311 is exposed to the outside through the opening of the front case 21 to form a contact surface with the skin. According to an embodiment, at least one sealing ring 313 is formed between the vibrator 311 and the front case 21, so that it can be prevented moisture or the like from permeating into the inside portion thereof through a gap between the vibrator 311 and the front case 21.

The vibrator 311 may generate ultrasonic vibrations based on a current applied under the control of the processor. For example, the vibrator 311 may generate ultrasonic vibration having a frequency of about 200 KHz to 500 KHz, but is not limited thereto. The ultrasonic vibration creates temporary cracks in the stratum corneum of the skin, so that micro dust or contaminants on the skin surface can be discharged to the outside of the skin, and the removal rate of dead skin cells present on the skin surface can be improved.

The vibration motor 32 may be driven under the control of the processor. As the vibration motor 32 is driven, the skin cleanser 1 may vibrate (vibrate finely) in the front and rear direction. In this case, micro-vibrations may be transmitted to the skin through the brush 322 in contact with the skin. When the micro-vibration is transmitted to the skin through the brush 322, the amount of foam generated by the cleaning agent applied to the skin surface (for example, facial cleansing foam or the like) increases, so that the cleaning power for contaminants or cosmetics present on the skin surface can be improved.

The brush bracket 321 may be formed in a ring shape. The brush bracket 321 may be fastened (mounted or attached) to a region of the outer surface of the front case 21 surrounding the opening through which the upper surface of the vibrator 311 passes.

A brush 322 may be fastened (mounted or attached) to the front of the brush bracket 321. The brush 322 may include protrusions made of a silicone material that is harmless to the human body. An opening through which the upper surface of the vibrator 311 passes is formed in the center of the brush 322, and thus the upper surface of the vibrator 311 is exposed to the outside through the opening to be in contact with the skin.

The brush 322 may transmit vibration to the skin by vibrating according to the driving of the vibration motor 32. By vibration of the brush 322, the amount of foam generated by the cleaning agent applied to the skin surface may increase, and contaminants attached to the skin surface may be effectively separated from the skin. Accordingly, it may be possible to effectively clean the skin.

According to an embodiment, the brush 322 may be attached to the brush bracket 321 through the adhesive member 323, and the brush bracket 321 may also be attached to the front case 21 through the adhesive member 324. For example, the adhesive member 323 may include various types of adhesives such as double-sided tape.

Meanwhile, as described above, the cover 201 may be formed to surround the front case 21 and the rear case 22. In this case, the inner surface of the cover 201 may be in close contact with the outer surface of the front case 21 and the outer surface of the rear case 22.

However, small amount of air may exist between the cover 201 and the cases 21 and 22. Alternatively, air may flow between the cover 201 and the cases 21 and 22 according to the use of the skin cleanser 1.

In this case, when the temperature rises according to a change in the environment around the skin cleanser 1, the air existing between the cover 201 and the cases 21 and 22 may expand. As the air expands, a phenomenon in which the cover 201, which has relatively high ductility compared to the cases 21 and 22, swells may occur. According to the above phenomenon, the aesthetics of the skin cleanser 1 may be impaired, and the user may have doubts about the reliability of the product, such as mistakenly thinking that water has permeated into the cover 201.

A structure for preventing swelling of a cover according to an embodiment of the present disclosure for solving the above-described problem will be described with reference to FIGS. 4 to 8.

FIG. 4 is an exemplary view illustrating the swelling phenomenon of the cover that occurs when the anti-swelling structure of the cover is not implemented according to an embodiment of the present disclosure.

Referring to FIG. 4, as described above, when the skin cleanser 1 or the surrounding temperature rises, small amount of air AIR existing between the case (rear case 22) and the cover 201 can expand.

The cover 201 may be implemented with a material having relatively high ductility compared to the cases 21 and 22. For example, the cases 21 and 22 may be implemented with a plastic material, and the cover 201 may be implemented with a silicon material.

In other words, when the expanded air AIR cannot be discharged to the outside, a phenomenon in which the cover 201 with relatively high ductility swells occurs. Accordingly, the aesthetics of the skin cleanser 1 may be impaired, and the user may have doubts about the reliability of the product, such as mistakenly thinking that water has permeated into the cover 201.

FIG. 5 is a view for explaining the anti-swelling structure of the cover according to an embodiment of the present disclosure. FIG. 6 is a view illustrating a state where air expanding between a cover and a case is discharged to the outside when the anti-swelling structure of FIG. 5 is implemented. FIG. 7 is a view illustrating a state where air is discharged to the outside through a speaker assembly and a speaker hole provided in a device according to an embodiment of the present disclosure. FIG. 8 is a view illustrating a membrane for preventing external moisture from permeating into the device while discharging air inside the device to the outside through the speaker hole.

Referring to FIG. 5, as described above with reference to FIG. 3, the speaker assembly 25 may be provided under the rear case 22.

The speaker assembly 25 may include a speaker 252 provided with a diaphragm for generating sound. For example, the speaker 252 may be implemented as a piezoelectric speaker having a metal diaphragm, but this is not necessarily the case.

Meanwhile, the rear case 22 may be formed with a resonator 253 amplifying sound waves generated according to the vibration of the diaphragm included in the speaker 252. For example, the resonator 253 may be formed in a substantially rectangular parallelepiped shape. In this case, the rear case 22 may form four of the six surfaces of the resonator 253. Among the remaining two surfaces, the speaker 252 may be fastened to the surface facing the speaker hole 264, and the resonator cover 251 may be fastened onto the other surface (for example, the surface facing the front case 21), via a screw sc or the like.

The speaker 252 may be disposed between the resonator 253 and the speaker hole 264. The speaker 252 may be implemented to have a waterproof function by itself, but this is not necessarily the case.

Meanwhile, according to an embodiment of the present disclosure, at least one opening 254 may be formed on a surface of the surfaces of the resonator 253 in contact with the cover 201. In other words, at least one opening 254 may be formed in an area of the rear case 22 between the cover 201 and the resonator 253.

The micro space between the cover 201 and the rear case 22 and the resonator 253 may be connected by the at least one opening 254. Accordingly, the expanded air AIR described above in FIG. 4 may move to the resonator 253 through the at least one opening 254 and may be discharged to the outside through the speaker hole 264. In other words, a phenomenon in which the cover 201 swells when the air AIR is expanded can be effectively prevented.

However, when the outer cover 201 is damaged (tear or the like), water may permeate between the cover 201 and the cases 21 and 22, and there is a possibility that the permeated water flows into the resonator 253 through the at least one opening 254. In this case, the performance of the speaker may be deteriorated or other components in the skin cleanser 1 may be damaged.

To prevent this, the first membrane 255 blocking the inflow of water may be provided in the region including the at least one opening 254. For example, the first membrane 255 may be attached to the outer surface of the rear case 22 including at least one opening 254, but is not limited thereto, and may be attached to the inner surface of the rear case 22 (resonator 253).

The first membrane 255 may be implemented with a moisture-permeable waterproof material that blocks moisture, such as water, and transmits air. For example, the first membrane 255 may be implemented with various materials (synthetic resin or the like) such as polyethylene (PE) and high density polyethylene (HDPE) in which micro-pores are formed through which water does not permeate and only air can pass.

Air AIR expanded between the cover 201 and the cases 21 and 22 may transmit the first membrane 255 and move to the resonator 253.

A speaker cover assembly 26 may be fastened to a lower side of the speaker assembly 25. For example, the speaker cover assembly 26 may include a speaker cover 261 fastened to the rear case 22 through a screw or the like from a lower side of the rear case 22. Accordingly, the speaker cover 261 may be disposed below the speaker 252.

The cover 201 may be formed to surround the cases 21 and 22 and the speaker cover 261. An opening may be formed in the speaker cover 261 in a vertical direction, and an opening may be formed in the cover 201 at a position corresponding to the opening of the speaker cover 261. In other words, the speaker hole 264 may be formed by the opening of the speaker cover 261 and the opening of the cover 201.

The speaker cover assembly 26 may further include a second membrane 262 disposed between the speaker cover 261 and the speaker 252. The second membrane 262 may contact a portion of a lower surface of the speaker 252 and a portion of an upper surface of the speaker cover 261.

Like the first membrane 255, the second membrane 262 may be implemented with a material that blocks moisture such as water and transmits air. Accordingly, water can be prevented from entering the inside through the speaker hole 264. In addition, the expanded air (AIR) between the cover 201 and the cases 21 and 22 transmits the first membrane 255 and moves to the resonator 253, and after transmitting the second membrane 262 between the speaker 252 and the speaker cover 261, the expanded air may be discharged to the outside through the speaker hole 264.

According to an embodiment, a sealing ring 263 may be further formed on the outer circumference of the upper surface of the speaker cover 261. The sealing ring 263 may seal the space between the speaker cover 261, the second membrane 262, and the rear case 22, thereby effectively blocking water from entering from the outside. In addition, the sealing ring 263 may be formed of a material such as silicon and rubber and may also block air permeation. Accordingly, since the air in the resonator 253 can be effectively discharged through the speaker hole 264, the sound generated by the speaker can be output more clearly.

Referring to FIGS. 7 to 8, air in the resonator 253 may move toward the second membrane 262 through a gap between the rear case 22 and the speaker 252.

For example, the speaker 252 may include a speaker main body 252a including a diaphragm, and a speaker fixing part 252b for fixing the speaker main body 252a to the lower side of the resonator 253 (rear case 22).

Meanwhile, a partial region of the contact region between the speaker 252 and the rear case 22 may be opened for the inflow and outflow of air. For example, an open region 252c is formed in at least one of the side edges of the speaker 252, and air in the resonator 253 is discharged to the outside through the open region 252c, or external air can flow into the resonator 253. Alternatively, an opening is formed in a partial region of the speaker 252 in the vertical direction, so that air may flow into the resonator 253 through the opening or discharged to the outside of the resonator 253.

Air discharged from the resonator 253 through the open region 252c may move to a gap region between the speaker main body 252a and the second membrane 262.

For example, the second membrane 262 may be divided into a permeable region 262a through which air transmits, and a contact region 262b formed outside the permeable region 262a. The permeable region 262a may be located in a region including the opening of the speaker cover 261. The permeable region 262a may be spaced apart from the speaker main body 252a by a predetermined distance to form a gap region between speaker main body 252a and the permeable region. Accordingly, when the diaphragm included in the speaker main body 252a vibrates, the problem that the diaphragm and the second membrane 262 come into contact with each other so that sound is not normally output or the second membrane 262 is damaged can be prevented.

The contact region 262b may correspond to a region in contact with (attached, adhered to, or the like) the speaker 252 and the speaker cover 261.

Meanwhile, a gap region between the speaker main body 252a and the second membrane 262 may be connected to the open region 252c. For example, a groove or channel connecting the gap region and the open region 252c may be formed in the speaker main body 252a. Alternatively, at least a partial region between the gap region and the open region 252c among the contact region 262b of the second membrane 262 may not be in contact with the speaker 252.

Accordingly, the air moved from the resonator 253 to the open region 252c may be moved to the gap region and may be discharged to the outside through the speaker hole 264 after transmitting the permeable region 262a.

In summary, air (AIR) between the cover 201 and the cases 21 and 22 may transmit the first membrane 255 and flows into the resonator 253. The air flowing into the resonator 253 may move to the open region 252c through an opening of the speaker 252 or a gap between the speaker 252 and the rear case 22. Air moved to the open region 252c moves to the gap region between the speaker main body 252a and the second membrane 262, transmits the permeable region 262a of the second membrane 262, and thus can be discharged to the outside through the speaker hole 264.

In other words, according to the embodiment of FIGS. 4 to 8, among the components received in the cover 201 or the cases 21 and 22 of the skin cleanser 1, only the speaker assembly 25 can be connected to the outside through the speaker hole 264. Accordingly, in the skin cleanser 1 according to an embodiment of the present disclosure, in order to discharge the expanded air between the cover 201 and the cases 21 and 22 to the outside, the space between the cover 201 and the cases 21 and 22 may be implemented to be connected to the resonator 253. In addition, in order to prevent moisture such as water from flowing into the resonator 253 from the outside, the above-described first membrane 255 and the second membrane 262 may be formed in the skin cleanser 1.

Accordingly, the swelling phenomenon of the cover 201 caused by the expansion of the air is eliminated, thereby preventing a decrease in the reliability of the user's product. In addition, by preventing moisture from flowing into the resonator 253, it is possible to prevent deterioration or damage to the speaker.

FIG. 9 is a view illustrating a sealing member constituting a waterproof structure of a device according to an embodiment of the present disclosure. FIG. 10 is a view for explaining a sealing member mounting part formed in the case of the device. FIG. 11 is a view illustrating a state where the sealing member is mounted to the sealing member mounting part illustrated in FIG. 10.

The membranes 255 and 262 described above in FIGS. 4 to 8 may correspond to a waterproof configuration of the speaker assembly 25.

Meanwhile, when the cover 201 is damaged and water flows between the cover 201 and the cases 21 and 22, there is a possibility that water flows between the front case 21 and the rear case 22. When water flows into the receiving space formed by the front case 21 and the rear case 22, there is a risk of damage to parts existing in the receiving space.

Referring to FIG. 9, a sealing member 27 may be provided between the front case 21 and the rear case 22. The sealing member 27 may be implemented with a material such as silicone and rubber having elasticity and ductility.

The sealing member 27 may be mounted to correspond to the shape of the coupling area between the front case 21 and the rear case 22. To this end, a sealing member mounting part may be formed on the front case 21 or the rear case 22.

Meanwhile, the sealing member 27 according to the embodiment of the present disclosure may include a sealing member main body 271 corresponding to the shape of the coupling area, and a plurality of sealing member mounting ribs 272 protruding inward or outward from a predetermined point of the sealing member main body 271, respectively.

Contents related to the components included in the sealing member 27 will be described in more detail with reference to FIGS. 10 to 11.

In FIGS. 10 to 11, the sealing member mounting part is illustrated as being formed on the front case 21, but according to an embodiment, the sealing member mounting part may be formed on the rear case 22.

Referring to FIG. 10, the sealing member mounting part may include a mounting groove 213 formed between the inner wall 212a and the outer wall 212b having a predetermined height. For example, the coupling region of the front case 21 and the rear case 22 may be a region having a substantially ring shape, and in this case, the mounting groove 213 may be formed in a ring shape corresponding to the coupling region. A fastening part 211 can be used to fasten the front case 21 to the rear case 22.

The sealing member main body 271 may be formed to correspond to the mounting groove 213 or may be deformable to correspond to the mounting groove 213. In other words, the sealing member main body 271 may also have a ring shape. As the sealing member main body 271 is inserted and mounted in the mounting groove 213 and the rear case 22 is fastened to the front case 21, the sealing member main body 271 can shield a receiving space between the front case 21 and the rear case from the outside.

Meanwhile, when the mounting groove 213 is not formed in a regular circular or regular polygonal shape (for example, an ellipse), the sealing member main body 271 must be inserted at a correct position when inserted into the mounting groove 213.

When the sealing member main body 271 is not inserted in the correct position, deviation (thickness deviation) for each position of the sealing member main body 271, such as a state where some areas of the sealing member main body 271 are stretched compared to other areas and become thinner may occur. Due to the deviation, a space that is not normally shielded by the sealing member 27 may be generated in the coupling region between the front case 21 and the rear case 22. In this case, as water permeates into the interior through the space during use of the skin cleanser 1, damage to parts received therein may occur.

In order to minimize the above-described problem, the sealing member 27 according to an embodiment of the present disclosure may include a plurality of sealing member mounting ribs 272 protruding inward or outward from each of predetermined points of the sealing member main body 271.

In addition, a plurality of rib mounting guides 214 may be formed in the sealing member mounting part. The plurality of sealing member mounting ribs 272 may be formed to correspond to the plurality of rib mounting guides 214.

Specifically, openings may be formed at a plurality of points of the inner wall 212a (or the outer wall 212b). The height of the wall 212a or 212b at the points where the opening is formed may be lower than the height of the wall 212a or 212b at other points. Alternatively, the walls 212a or 212b may not be formed at points corresponding to the plurality of openings.

The plurality of sealing member mounting ribs 272 may be mounted to correspond to the plurality of openings, respectively. In other words, the plurality of openings may correspond to the plurality of rib mounting guides 214.

When the plurality of rib mounting guides 214 are formed on the inner wall 212a, the plurality of sealing member mounting ribs 272 may be formed to protrude inward from the sealing member main body 271. On the other hand, when the plurality of rib mounting guides 214 are formed on the outer wall 212b, the plurality of sealing member mounting ribs 272 may be formed to protrude outwardly from the sealing member main body 271.

As the plurality of rib mounting guides 214 and the plurality of sealing member mounting ribs 272 are formed, the sealing member main body 271 may be inserted at a correct position when inserted into the mounting groove 213. As a result, since the occurrence of a thickness deviation for each position of the sealing member main body 271 is prevented, effective waterproofing of the receiving space between the front case 21 and the rear case 22 may be made possible.

In addition, even if there is a product deviation (size, shape, or the like) for each of the sealing member 27, since the insertion position of the sealing member 27 is set by the rib mounting guide 214 and the sealing member mounting rib 272, the phenomenon that the sealing member 27 is not inserted in the correct position due to product deviation can also be minimized.

FIGS. 12 to 13 are views illustrating modified examples of the sealing member according to the height of the mounting groove of the sealing member mounting part.

Referring to FIGS. 12 to 13, according to the thickness of the sealing member main body 271 and the depth of the mounting groove 213 (or the height of the inner wall 212a and the outer wall 212b), the waterproof performance of the space between the front case 21 and the rear case 22 may vary. Hereinafter, for convenience of description, it is assumed that the cross-section of the sealing member main body 271 is circular.

FIG. 12(a) is a view illustrating a case where the depth H1 of the mounting groove 213 is equal to or greater than the cross-sectional radius H2 of the sealing member main body 271, and FIG. 12(b) is a view illustrating a case where the depth H3 of the mounting groove 213 is smaller than the cross-sectional radius H2 of the sealing member main body 271.

Referring to FIGS. 12(a) and 13(a), the depth H1 of the mounting groove 213 is greater than or equal to the cross-sectional radius H2 of the sealing member main body 271 (or at least half of the cross-sectional height of the sealing member body 271), sufficient space for the sealing member main body 271 to be inserted may be secured.

In other words, when the front case 21 and the rear case 22 are fastened, the sealing member main body 271 is stably received in the mounting groove 213, and thus the receiving space between the front case 21 and the rear case 22 can be effectively shielded from the outside.

On the other hand, referring to FIGS. 12(b) and 13(b), when the depth H3 of the mounting groove 213 is less than the cross-sectional radius H2 of the sealing member main body 271, the sealing member main body 271 may not be effectively received in the mounting groove 213.

In this case, when the front case 21 and the rear case 22 are fastened, a portion of the sealing member main body 271 may deviate to the outside of the mounting groove 213. Accordingly, the receiving space between the front case 21 and the rear case 22 may not be completely shielded from the outside, causing a problem that water permeates into the receiving space.

Therefore, the mounting groove 213 according to the embodiment of the present disclosure is formed to have a sufficient depth for receiving the sealing member main body 271, and thus effective waterproof performance can be provided in the receiving space between the front case 21 and the rear case 22.

The above description is merely illustrative of the technical spirit of the present disclosure, and various modifications and variations will be possible without departing from the essential characteristics of the present disclosure by those skilled in the art to which the present disclosure pertains.

Therefore, the embodiments disclosed in the present disclosure are not intended to limit the technical spirit of the present disclosure, but to explain, and the scope of the technical spirit of the present disclosure is not limited by these embodiments.

The protection scope of the present disclosure should be interpreted by the following claims, and all technical ideas within the scope equivalent thereto should be construed as being included in the scope of the present disclosure.

The invention claimed is:

1. A device comprising:
   a case having a receiving space formed therein;
   a cover configured to surround the case;
   a speaker assembly configured to be mounted on the case, the speaker assembly including a speaker, a diaphragm, and a resonator formed on one side of the speaker;
   a speaker hole configured to be connected to the speaker assembly,
   wherein the case includes at least one opening formed between the resonator and a space between the cover and the case; and
   a speaker cover in which an opening corresponding to the speaker hole is formed and locating the speaker between the resonator and the speaker cover.

2. The device of claim 1, further comprising:
   a membrane formed in a region that includes the at least one opening,
   wherein the membrane is implemented with a moisture-permeable and waterproof material.

3. The device of claim 2, wherein the membrane is attached to the region that includes the at least one opening among an outer surface of the case.

4. The device of claim 1, wherein the cover includes an opening formed at a position corresponding to the opening of the speaker cover.

5. The device of claim 1, further comprising;
   a membrane formed between the speaker cover and the speaker,
   wherein the membrane is implemented with a moisture-permeable and waterproof material.

6. The device of claim 5, wherein the membrane is divided into a permeable region located in the region that includes the opening of the speaker cover, and a contact region formed outside the permeable region, and
   wherein the contact region is an area in contact with the speaker and the speaker cover.

7. The device of claim 6, wherein the permeable region is spaced apart from the speaker by a predetermined distance.

8. The device of claim 7, wherein a gap region between the speaker and the permeable region is connected to the resonator through a groove formed in the speaker or a space between the speaker and the case.

9. The device of claim 1, wherein the cover is implemented with a material having a higher ductility than the case.

10. The device of claim 9, wherein the case is implemented with a plastic material, and
wherein the cover is implemented with a silicone material.

11. A device comprising:
a case having a receiving space formed therein;
a cover configured to surround the case;
a speaker assembly configured to be mounted on the case, the speaker assembly including a speaker, a diaphragm, and a resonator formed on one side of the speaker; and
a speaker hole configured to be connected to the speaker assembly,
wherein the case includes at least one opening formed between the resonator and a space between the cover and the case,
wherein the case includes:
a first case;
a second case fastened to the first case to form the receiving space between the first case and the second case; and
a sealing member mounted between the first case and the second case, and
wherein a mounting groove in which the sealing member is mounted is formed in the first case or the second case.

12. The device of claim 11, wherein the sealing member includes:
a ring-shaped sealing member main body corresponding to the mounting groove; and
a plurality of sealing member mounting ribs configured to protrude inwardly or outwardly from each of a plurality of points of the sealing member main body, and
wherein a plurality of rib mounting guides corresponding to the plurality of sealing member mounting ribs are formed in the mounting groove.

13. The device of claim 12, wherein the mounting groove is defined by an inner wall and an outer wall formed at a predetermined height along a coupling area of the first case and the second case,
wherein the plurality of rib mounting guides are defined by an opening formed at a plurality of points of the inner wall or the outer wall, and
wherein a height of the wall at each of the plurality of points where the opening is formed is lower than a height of the wall at the other points.

14. The device of claim 11, wherein a depth of the mounting groove is at least half a height of a cross-section of the sealing member.

15. A device comprising:
a case having a receiving space formed therein;
a cover configured to surround the case;
a speaker assembly configured to be mounted on the case, the speaker assembly including a speaker, a diaphragm, and a resonator formed on one side of the speaker;
a speaker hole configured to be connected to the speaker assembly;
an ultrasonic vibrator;
a vibration motor; and
a brush,
wherein the case includes at least one opening formed between the resonator and a space between the cover and the case,
wherein an opening through which at least a part of the ultrasonic vibrator received in the receiving space passes is formed in the case, and
wherein the brush is fastened to the case and has a donut shape surrounding an outer circumference of the ultrasonic vibrator.

* * * * *